United States Patent [19]
Spivey et al.

[11] Patent Number: 5,417,218
[45] Date of Patent: May 23, 1995

[54] ACOUSTIC IMAGING DEVICE

[76] Inventors: Brett A. Spivey, 131 Seeman, Encinitas; Peter J. martin, 1819 Avenida Mimosa, both of Encinitas, Calif. 92024; Douglas A. Palmer, 1229 Triesta Dr., San Diego, Calif. 92167; Robert Cram, 2348 Black Canyon, Ramona, Calif. 92065

[21] Appl. No.: 232,740

[22] Filed: Apr. 25, 1994

Related U.S. Application Data

[63] Continuation-in-part of Ser. No. 891,851, Jun. 1, 1992, Pat. No. 5,305,752, which is a continuation-in-part of Ser. No. 708,354, May 31, 1991, abandoned.

[51] Int. Cl.6 .......................... A61B 8/00; G01N 29/00
[52] U.S. Cl. .................................. 128/661.02; 73/602
[58] Field of Search ............... 128/661.02, 660.01, 128/660.07, 661.01, 916; 73/602; 367/103; 364/413.25

[56] References Cited

U.S. PATENT DOCUMENTS

| | | | |
|---|---|---|---|
| 4,222,274 | 9/1980 | Johnson | 128/661.01 |
| 4,562,540 | 12/1985 | Devaney | 128/916 X |
| 4,594,662 | 6/1986 | Devaney | 128/916 X |
| 4,598,366 | 7/1986 | Devaney | 128/916 X |
| 4,662,222 | 5/1987 | Johnson | 73/602 |

*Primary Examiner*—Francis Jaworski
*Attorney, Agent, or Firm*—John R. Ross

[57] ABSTRACT

This invention provides an acoustic imaging device in which a large number of transducers are spaced less than a half acoustic wavelength apart on a circle surrounding an object to be imaged. A signal generator generates discrete acoustic frequencies in the range of 100 kHz to 1.5 MHz. Multiplexer systems are provided to permit each transducer, one at a time, to broadcast a signal while the broadcast signal is detected by the other transducers. Electronic equipment records the detected signal and from the recorded information phase and amplitude data is calculated with respect to each transducer location. A computer programmed with an algorithm computes images of slices through the object using the phase and amplitude data. We utilize single frequency, steady-state acoustic signals which enables the accurate determination of the phase and amplitude of the acoustic signals at each receiver transducer. Finally, in order to reduce the data acquisition time and reduce motion artifacts, we utilize acoustic signals comprised of a plurality of discrete indentifiable frequencies each frequency providing an image of the medium.

18 Claims, 15 Drawing Sheets

ACOUSTIC IMAGING DEVICE

BACKGROUND OF THE INVENTION

This application is a continuation in-part of Ser. No. 07/891,851 filed Jun. 1, 1992, and now U.S. Pat. No. 5,305,752 which is a continuation in part of Ser. No. 07/708,354 filed May 31, 1991, now abandoned.

This invention relates to imaging systems and methods and in particular to systems and methods for creating internal images of objects using mathematical procedures and acoustic wave data.

In conventional fan beam transmission tomography, such as utilized in x-ray computed tomography (x-ray CT), the attenuation of a fan beam of x-rays is measured as this beam probes medium along many different trajectories. The information contained in these attenuation projections is then used to reconstruct a tomographic image of the medium. The success of x-ray CT (manifested in the resolution and clarity of the images) is fundamentally linked to the very short wavelength of the incident x-ray beam ($\approx 1$ Å). The mathematical reconstruction techniques assume a geometrical ray approximation and are quite simplified.

In ultrasonic tomography, the acoustic wavelengths ($\approx 1$ mm) are on the order of the scale size of the inhomogeneities of the medium and the diffraction effects of the acoustic wave are not negligible. In this case, the attenuation of a sound wave is substantially affected by scattering effects such as diffraction, refraction, and reflection, as well as absorption. The simplified mathematical reconstruction algorithms used in conventional x-ray CT are not applicable in this case.

Ultrasonic diffraction tomography (UDT) techniques attempt to mathematically reconstruct a tomographic image of a medium from acoustic wave data with full consideration to the scattering effects associated with acoustic wavelengths involved. This is done by considering the full wave equation, a much more difficult problem to develop and implement than the geometrical wave approximation reconstruction methods used in x-ray CT. UDT techniques attempt to determine the internal structure of an object which is semi-transparent to acoustic waves from a set of scattered wave data detected outside at the boundary of the object. A number of these mathematical techniques have been theoretically considered, including simplified algorithms which use the Born approximation (E. Wolf, "Three-dimensional Structure Determination of Semi-Transparent Objects from Holographic Data", Opt. Comm. 153–156 (1969)) and Rytov approximations (A. J. Devaney, "Inverse Scattering Within the Rytov Approximation", Opt. Lett. 6, 374 (1981)). The Born and Rytov approximations assume that the medium which is imaged is a weak scatterer of acoustic waves and that the acoustic wave does not experience large phase shifts within the medium. Computer intensive full-wave reconstruction algorithms (S. Johnson and M. Tracy, "Inverse Scattering Solutions By a Sinc Basis, Multiple Source, Moment Method", Ultrasonic Imaging 5, 361–375 (1983) and references therein) have also been proposed for imaging mediums under conditions which are not in the range of validity of the Born or Rytov approximation.

Prior art patents included Devaney (U.S. Pat. Nos. 4,598,366 and 4,594,662) and Johnson (U.S. Pat. No. 4,662,222). The patents of Johnson disclose iterative algorithms which form an initial estimate of the sound speed at all points within the object being imaged, calculate a sound speed map (a type of image), and then update the map. This process is repeated until a residual error parameter is small enough. The patents of Devaney form an image directly from the data using Born and Rytov inversions with a technique called filtered back propagation.

SUMMARY OF THE INVENTION

It is an object of the present invention to provide a system and method to insonify a medium with ultrasonic waves, record information relating to ultrasonic waves scattered from the medium and use that information to quickly and efficiently construct images of the medium.

The present invention provides an acoustic imaging device in which a large number of transducers are spaced less than a half acoustic wavelength apart on a circle surrounding an object to be imaged. A signal generator generates discrete acoustic frequencies in the range of 100 kHz to 1.5 MHz. Multiplexer systems are provided to permit each transducer, one at a time, to broadcast a signal while the broadcast signal is detected by the other transducers. Electronic equipment records the detected signal and from the recorded information phase and amplitude data is calculated with respect to each transducer location. A computer programmed with an algorithm computes images of slices through the object using the phase and amplitude data. We utilize single frequency, steady-state acoustic signals which enables the accurate determination of the phase and amplitude of the acoustic signals at each receiver transducer. Finally, in order to reduce the data acquisition time and reduce motion artifacts, we utilize acoustic signals comprised of a plurality of discrete indentifiable frequencies each frequency providing an image of the medium.

DETAILED DESCRIPTION OF PREFERRED EMBODIMENTS

This invention provides a system for insonifying a medium with acoustic waves at discrete frequencies from a plurality of locations, and for recording data representing acoustic waves scattered from the medium. Algorithms are provided for calculating images of the medium from the recorded data.

A. Description of Instrumentation

Figure 1:
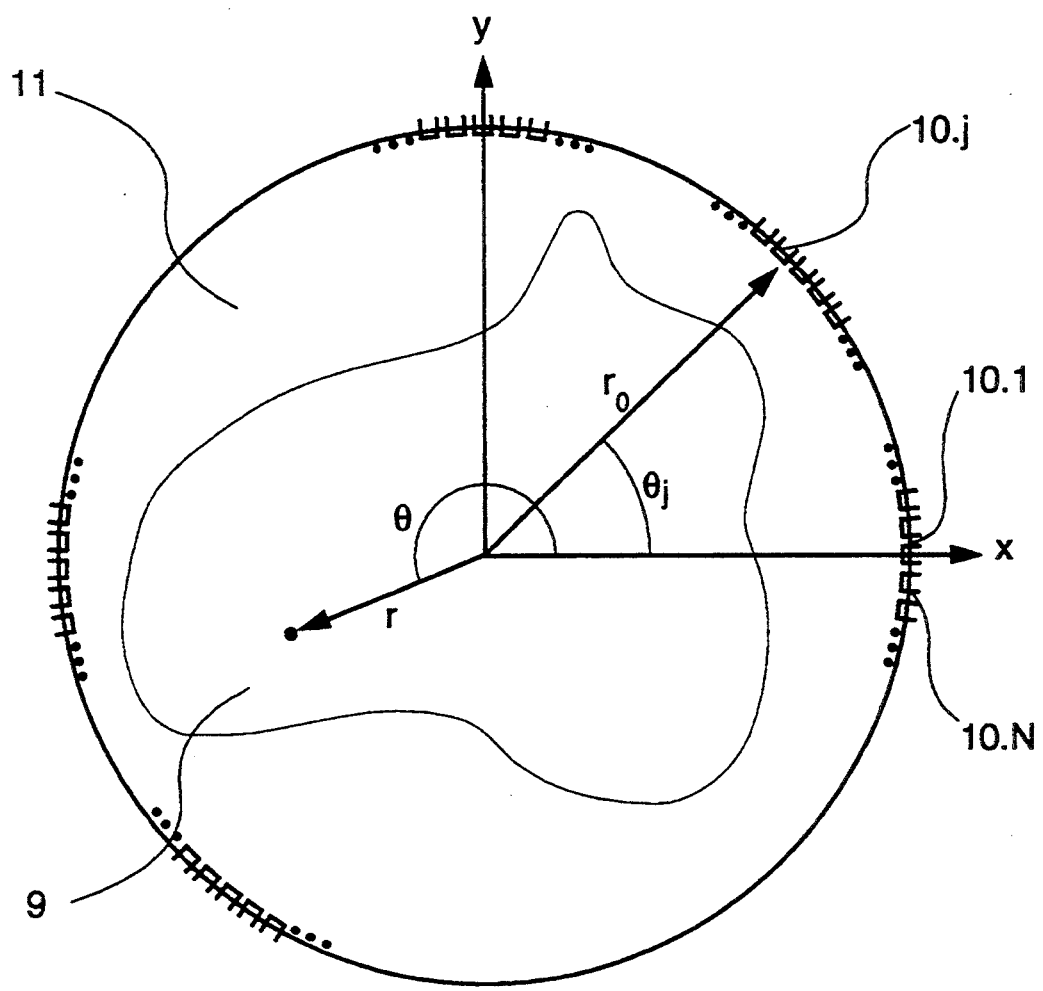
FIG. 1 is a schematic diagram for use in illustrating the mathematical reconstruction algorithm.

A schematic diagram of the cross-section of a portion of a preferred embodiment and an object being imaged is shown in FIG. 1. In this embodiment, there are 1024 acoustic transducers 10 or 10.1, . . . ,10.1024 evenly arranged on the locus of a circle of radius $r_o = 102$ mm. The transducers 10, each which can act as either a transmitter or a receiver of acoustic waves, are located in a thin slice approximating a plane which we call the $(r,\theta)$ (or $(x,y)$) plane. The z-direction is perpendicular to this plane. The transducers circumscribe object 9 which is assumed to be semi-transparent to the acoustic waves. In the preferred embodiment, a coupling fluid 11 resides in the remaining volume (shown as an area) inside the circle to effectively couple acoustic waves between the transducers 10 and object 9. The object 9 and the coupling fluid 11 in the remaining volume is herein referred to as medium 12. Water is a preferred fluid for imaging human tissue because water and human tissue have approximately equal sound speed and density. When imaging other objects, a coupling fluid 11 should be chosen which preferably has a density $\rho_o$ and sound speed $c_o$ which are approximately equal to the average density and sound speed of the object 9 being imaged (salt water is sometimes better than pure water for use with human tissue).

In a preferred embodiment of the present invention, each acoustic transducer 10 has a 1 MHz center frequency, a 60% bandwidth, and each performs at different times as a receiver or a transmitter of acoustic waves. At a 1 MHz frequency, the acoustic wavelength $\lambda_o = 1.5$ mm in water and approximately this wavelength in human tissue. The spacing between transducers is 0.65 mm which is somewhat less than $\lambda_o/2$ in water in order to provide adequate sampling of the scattered wavefront (i.e. to avoid aliasing). This facilitates the construction of unique images from the acquired data. In this preferred embodiment, each transducer has a dipole radiation pattern in the $(r,\theta)$ plane. The vertical height of the transducers 10 is 12 mm and each transducer produces a beam which is approximately collimated in the z-direction for distance in the z direction of approximately 12 mm and propagates from the transducer in the $(r,\theta)$ plane. We thus insonify an effective thickness across the medium roughly equal to the vertical height of the transducers so that any image obtained could be expected to represent an average of scatter information over the height of the transducers (i.e. a slice about 12 mm thick).

Figure 2:
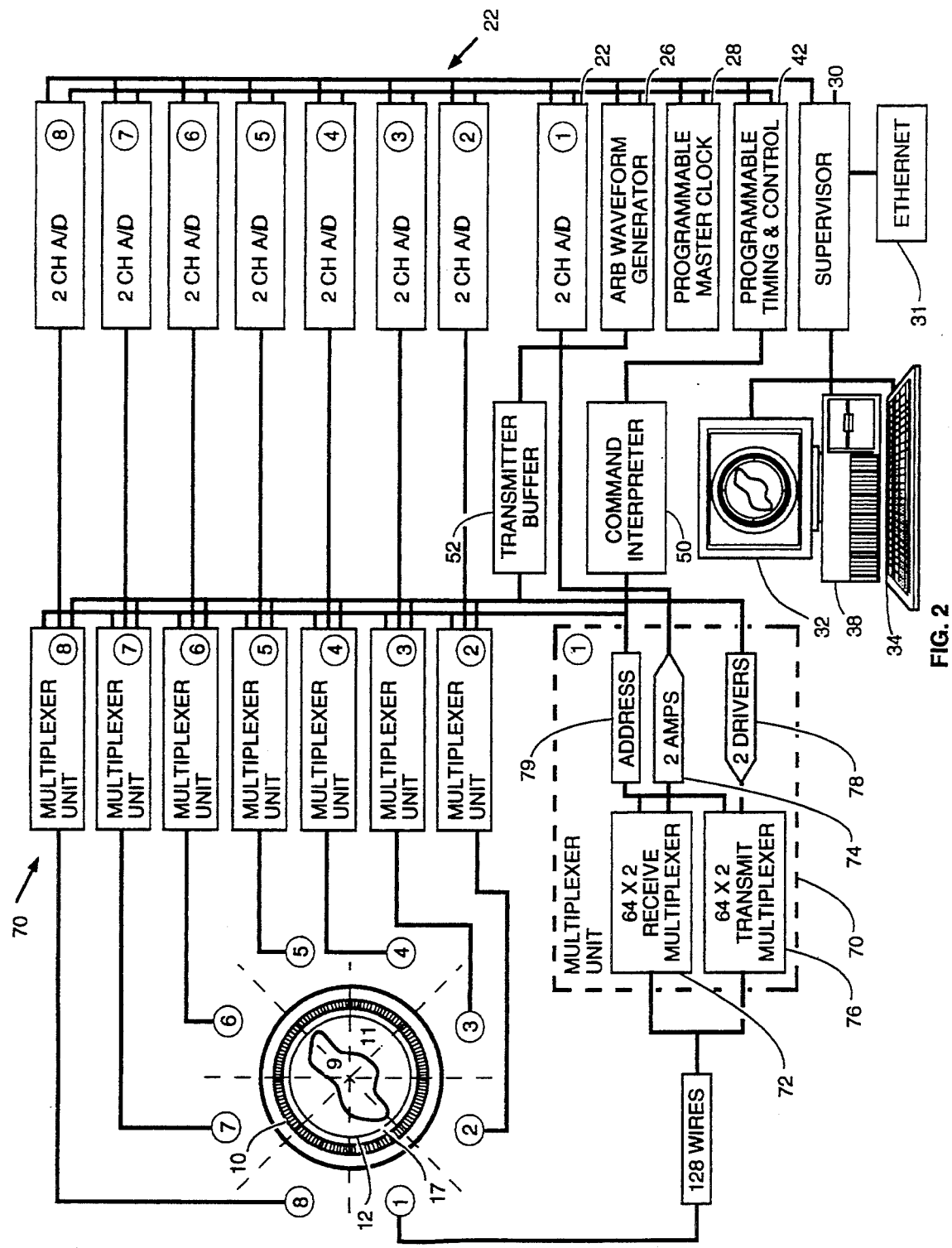
FIG. 2 is a block diagram of the electrical circuitry used in an actual prototype device of the invention.

A schematic diagram of our existing laboratory system is displayed in FIG. 2. The transducer ring 10 consists of 1024 acoustic transducers 10.1, . . . ,10.1024 arranged in a circle having a radius of 102 mm. The transducer ring 10 is divided into eight octants designated as octants 1 through 8, each octant containing 128 transducers. Connected to the ring are eight multiplexer sets 70 each multiplexer set consisting of a two-channel 64-to-1 receiver multiplexers 72, two amplifiers 74 each amplifier connected to one channel of the two-channel multiplexer, a two-channel 64-pin transmit multiplexer 76, two drivers 78 each driving one channel of the two channel transmit multiplexers, and an address decoder unit 79. The data is collected by eight two-channel analog-to-digital converter units 22 each having 16 megabytes of buffer memory. The system timing is accomplished by a programmable master clock 28 which drives programmable timing and control unit 42 and a phase-locked arbitrary wave form generator 26. The entire system is controlled by a supervisor computer unit 30 the supervisor having associated with it a high resolution monitor 32, a keyboard 34, a 3 gigabyte hard drive 38, and an ethernet link 31. Timing commands are communicated to the transducer multiplexer sets 70 through a command interpreter 50. The transmitter signal is generated by the arbitrary waveform generator 26 through a transmit buffer 52 and to the transducer multiplexers 70.

The individual components of the described preferred system are described in detail here:

1) Transducers

The transducers 10 used in our system are constructed from composites of piezoelectric and non-piezoelectric materials. Each acoustic transducer has a 1 MHz center frequency, a 60% bandwidth, and each performs at different times as a receiver or a transmitter of acoustic waves. At a 1 MHz frequency, the acoustic wavelength $\lambda_o = 1.5$ mm in water and approximately this wavelength in human tissue. The spacing between centerlines of adjacent transducers is somewhat less than $\lambda_o/2$ in water in order to provide adequate sampling of the scattered wavefront (i.e. to avoid aliasing). In addition, because the width of each transducer is less than $\lambda_o/2$, each transducer has a dipole antenna pattern in the $(r,\theta)$ plane. This means that the relative amplitude of the transmitted acoustic energy follows a $\cos \psi$ function of the angle $\psi$ measured relative to the vector normal to the surface of the transducer face. There are two acoustic impedance matching layers 17 between the transducers 10 and the coupling fluid 11. These layers help to couple acoustic energy from the transducers 10 to the coupling fluid 11. In addition, these layers 17 help to minimize the amount of acoustic energy reflected from the faces of the transducers 10 back into the medium 12. This reflected acoustic energy manifests itself as image artifacts in the final images of the medium 12. Several variations in transducer fabrication could be utilized instead of composites of piezoelectric and non-piezoelectric materials. These include transducers constructed from piezoelectric zirconate titanate (PZT5A, for example), piezoelectric film (PVDF), or co-polymers.

2) Transmitter and Receiver Multiplexers

Transmitter and receiver multiplexer and units are preferably fabricated from standard off-the-self multiplex equipment commonly used in communication equipment. We use Analog Device Inc. ADG506 devices and Com-Linear CLC522 devices.

3) Address Decoder

Our address decoder 79 is a model EP910 programmable logic device supplied by Altera Corporation. This unit is programmed to operate multiplexers 72 and 76.

4) Command Interpreter

Command interpreter 50 receives commands from programmable timing and control module 42 and transmits those commands to the address decoders 79 in multiplexer units 70 in order to activate both the transmitting and receiving transducers. For the command interpreter 50, we use type EP1810 programmable logic devices supplied by Altera Corp.

5) Programmable Master Clock

The programmable master clock 28 is a computer programmable generator capable of precisely generating a known clock frequency for the system. This component 28 generates the master time base that phase locks every element of the system and is set when the system is initialized for the data collection algorithm in use. The programmable master clock 28 is a VXI module of model number 1391 supplied by WaveTek Corporation.

8) Programmable Timing and Control Module

The BMC programmable timing and control module 42 is built around an Advance Micro Devices Corporation IDT 2910 micro sequencer. The module consists of a programmable bit slice micro-sequencer and micro instruction RAM that is clocked by the programmable master clock 28. This device is designed to generate a unique bit pattern on each successive clock cycle. It is used to initialize the multiplexers, control the command interpreter, produce sample clocks to the analog-to-digital converters 22, trigger the arbitrary wave form generator and enable data collection. Since the module is locked to the time base generator, all of these functions are phase locked operations. The module is designed to interface with the VME bus chassis of supervisor 30 as described below.

6) Arbitrary Waveform Generator

Our arbitrary waveform generator 26 is a phase locked computer programmable generator capable of producing the various arbitrary analog output waveforms necessary for various data acquisition methods. It is used to synthesize the waveform which is transmitted through the transducers 10 into the medium 12. Since it is phase locked to the programmable master clock 28 and triggered by the programmable timing and control module 42, the transmitted wave form is phase locked to the data collection sequence. Our arbitrary waveform generator 26 is a VXI module of model number 1395 supplied by Wavetek Corporation.

7) Analog-to-Digital Converters

The design of the analog-to-digital converters 22 is centered around the model SPT 7922 12 bit, 30 MHz analog-to-digital converters supplied by Signal Processing Technologies. Each channel contains 8 megabytes of local buffer memory. The converters 22 are programmed to collect the analog data received via receive multiplexers 72 and temporarily store this data in the digital buffer memory. The preferred system has 16 channels of analog-to-digital conversion which has a capacity to store 128 megabytes of data.

9) Computer Supervisor

The overall control of the imaging device is provided by computer supervisor 30. Supervisor 30 is used to initialize the system, compile and download timing and control algorithms, perform test functions, collect raw data and perform the data reduction algorithm producing the final image. Interface to the machine is provided by a keyboard 34 and monitor 32. A 3 gigabyte hard drive 38 is provided for data storage. An ethernet link 31 is provided from the machine to download or upload data and algorithms for subsequent off line processing and reduction. The supervisor 30 is a series of board level products from Radisys Corporation based on the Intel 80486 computer family and a compiler supplied by Zortech Corporation.

10) Important Elements

Images obtained with prototype devices built by the inventors and their co-workers are reproduced in FIGS. 8 through 11. These images and the specific algorithms we used to obtain the images are discussed in detail in subsequent sections of this patent. Applicants believe that their images are the best, by far, tomographic images ever obtained with an acoustic devices.

The principle advantages of the present system that has led to these improvements over the prior art are the combination of the following hardware elements:

1. A large number of transducers spaced generally less than $\lambda/2$ apart on a circle surrounding the object where $\lambda$ is the acoustic wavelength in the medium 12.
2. A choice of acoustic frequencies between 100 kHz and 1.5 MHz which allows the acoustic wave to traverse human tissue such as the female breast with a greatly reduced amount of distortion to the phase front of the incident acoustic wave (compared to acoustic waves used in the prior art with frequencies in the range of 3 to 10 MHz). The acoustic frequencies in the preferred embodiment are low enough to enable the reconstruction algorithms to more accurately calculate a final image from the acquired data. However, the acoustic frequencies are high enough to provide adequate spatial resolution in the final image. Also, the use of acoustic frequencies in the range of 100 kHz to 1.5 MHz results in a minimal amount of attenuation of the incident acoustic wave thus enabling the production of a single large format image of a large portion of tissue.
3. The use of discrete frequency, steady-state insonification of the medium 12 which allows an accurate measurement of the phase and amplitude of the acoustic wave for each discrete frequency at each receiver transducer.
4. The capability of recording quickly and storing a very large amount of acoustic data in order to develop the matrices of data from which the images can be calculated.
5. An electronic system for phase locking all aspects of the acoustic data generation and collection.

B. Description of Data Acquisition Process

The data acquisition process involves the systematic insonification of the medium 12 by having each transducer $10.j$ ($j=1, \ldots, N$) sequentially perform as transmitter of continuous wave, single frequency sound (frequency $\omega_1$) with subsequent reception of the scattered waves by the remaining transducers $10.k$ ($k=1, \ldots, N$;

k N j). The acquired information is in the form of an N×N complex matrix with $(N-1)^2$ coefficients which we call $m_{jk}(\omega_\alpha)$ (j,k=1, . . . ,N) for data acquired at insonification frequency $\omega_\alpha$. The $(N-1)^2 = 1023^2$ coefficients $m_{jk}(\omega_\alpha)$ (j,k=1, . . . ,N; jNk) may be collected as described in the following example.

The object 9 to be imaged such as a female breast is placed within transducer ring 10. A coupling fluid 11 is placed between the object 9 and transducer ring 10. With an operator signal from keyboard 34, individual components of the system are initialized by computer supervisor 30. The operator initiates a command to the programmable timing and control module 42 to start the acquisition sequence. Timing and control module 42 sends a sequence of commands to command interpreter 50 causing a reset of the transmitter and receiver multiplexers 60 to their initial state.

Arbitrary wave form generator 26 is then triggered which causes the first transmitter 10.1, through transmit multiplexers 76, to broadcast a single frequency ($\omega_1$=687 kHz) sinusoidal acoustic signal into the medium 12. The transmitted acoustic wave scatters from the inhomogeneities of medium 12 and impinges upon the other N−1 transducers 10.2 . . . 10.1024 which transform these acoustic signals into single frequency electrical signals. After a time T=270 microseconds corresponding to twice the transit time of the acoustic wave across the diameter 2 $r_o$ of the device, the acoustic signals at each transducer have reached a steady-state condition. At this time, the electrical signals from each transducer 10.2 to 10.1024 are routed to the eight two-channel analog-to-digital converters 22 through receive multiplexers 72. The exact data acquisition process for each transducer 10 proceeds as follows. The supervisor 30 instructs the programmable timing and control module 42 to take four quadrature measurements from each transducer 10.2 to 10.1024. These four measurements labeled A,B,C, and D are of the transducer voltage output at four short equally spaced intervals during one acoustic period which is phase locked to the signal from the arbitrary waveform generator 26. For example, if the input frequency is 1 MHz (with a period of $1 \times 10^{-6}$ second) samples are taken at $0.25 \times 10^{-6}$ second intervals. The real part of complex amplitude is determined by subtracting measurement B from D and the imaginary part is determined by subtracting measurement A from C. The calculated complex amplitude at each transducer contains the phase and amplitude information of the acoustic wave at each transducer 10.2 to 10.1024 as compared to the input signal from 10.1. The data is stored temporally in the buffer memory units of the analog-to-digital converter units 22.

The system has eight two-channel analog-to-digital converters so signals are recorded from the transducers 10 in parallel. First signals from sixteen transducers 10.2, 10.66, 10.129, . . . ,10.961 are recorded simultaneously. After acquiring data from the sixteen transducers 10.2, 10.66, 10.129, . . . ,10.961, the receive multiplexers 72 rout signals from the sixteen transducers 10.3, 10.67, 10.130, . . . ,10.962 to the analog-to-digital converters 22 which acquire data from these transducers. The acquisition process continues until each analog-to-digital converter 22 has acquired data from sixty-four transducers 10. This process takes 270 microseconds for the signals to reach steady-state and 512 microseconds for each analog-to-digital converter 22 to acquire samples from sixty-four transducers 10. Digital values representing the phase and amplitude of each receiving transducer 10.2, . . . ,10.1024 relative to the transmitting transducer 10.1 are recorded in the buffer memory of the analog-to-digital converters 22 as N−1 (i.e. 1023) complex coefficients $m_{jk}(\omega_1)$ (j=1; k=2, . . . ,1024). The data collection procedure continues by routing the $\omega_1$=687 kHz electrical signal to transducer 10.2 which now acts as a transmitter of the acoustic energy. After another time T=270 microseconds required for the system to reach a steady-state condition, electrical signals are sequentially measured from the transducers 10.1,10.3, . . . ,10.1024 as described above in order to collect 1023 complex coefficients $m_{jk}$ (j=2; k=1,3, . . . ,1024). The measurement procedure continues until each transducer 10.1, . . . ,10.1024 has acted as a transmitter of the acoustic wave. At this point, a complete set of data representing complex coefficients $m_{jk}(\omega_1)$ (j,k=1, . . . ,N; j N k) has been recorded for the frequency $\omega_1$=687 kHz. A full set of data at a single acoustic frequency is obtained in approximately 1 second. In the preferred embodiment, the entire preceding measurement procedure is repeated ten times in order to acquire a separate $m_{jk}(\omega_\alpha)$ at each of ten discrete frequencies $\omega_\alpha$ ($\alpha$=1,2, . . . ,10) spaced at 62.5 kHz intervals from 687 kHz to 1.250 MHz.

In order to initially calibrate the device, we acquire a complete set of data from the medium 12 with no object 9 (only the coupling fluid 11). This data will only be used to calibrate the transducers as described in Section D.1. The object 9 is removed and the entire measurement procedure described in the previous paragraph is repeated to acquire $m_{jk}^{incident}(\omega_\alpha)$ (j,k=1, . . . ,N;j≠k) for the medium 12 with no object 9 (only the coupling fluid 11) at each of ten discrete frequencies $\Omega_\alpha$ ($\alpha$=1,2, . . . ,10) spaced at 62.5 kHz intervals from 687 kHz to 1.250 MHz.

C. Calculation of an Image from the Acquired Data

The data $m_{jk}(\omega_\alpha)$ (j,k=1, . . . ,N;$\alpha$=1,2, . . . ,10) acquired for medium 12 is uniquely determined by the sound speed $c(r,\theta)$ and attenuation coefficient $\mu(r,\theta)$ of the medium. Our objective is to use this set of data $m_{jk}(\omega_\alpha)$ to calculate mathematically with a digital computer an image of a 12 mm thick slice of medium 12. This image is based on the calculation of an approximation of the complex scattering potential, $S^{(\alpha)}(r,\theta)$, at all locations $(r,\theta)$ throughout a 12 mm thick slice of the medium (see FIG. 1 ).

In the preferred embodiment, we calculate an image of the medium 12 from the acquired data $m_{jk}(\omega_\alpha)$ at each frequency $\omega_\alpha$. This image, defined as $S^{(\alpha)}(r,\theta)$, is a two-dimensional map of the medium 12. The third dimension is averaged over the vertical extent of the transducers 10.

Our algorithm for $S^{(\alpha)}(r,\theta)$ is derived from the well known acoustic wave equation known as the Helmholtz equation:

$$\nabla^2 f(r,\theta) + S^{(\alpha)}(r,\theta) f(r,\theta) = 0 \qquad (1)$$

where:

$$f(r,\theta) = \frac{\rho(r,\theta)}{\rho(r,\theta)^{\frac{1}{2}}}$$

a single frequency acoustic pressure wave $p(r,\theta)$ at frequency $\omega_\alpha$.

$\rho(r,\theta)$ is the density distribution in the medium.

$S(r,\theta) = k^2(r,\theta) - k_o^2 - \rho(r,\theta)^{\frac{1}{2}} \nabla^2 \rho(r,\theta)^{-\frac{1}{2}}$ is the complex scattering potential of the medium.

$\omega_\alpha$ = angular frequency of acoustic wave.

$k_0 = \omega_\alpha/c_o$ $c_o$ = sound speed in coupling fluid 11

$k(r,\theta) = [\omega_\alpha^2/c^2(r,\theta) - i\omega N(r,\theta)]^{\frac{1}{2}}$ is the complex wavevector which accounts for the spatially varying sound speed $c(r,\theta)$ and includes an acoustic energy loss term $N(r,\theta)$ which accounts for viscous heating of the medium 12 and diffraction of acoustic energy from the field of view of the transducers 10.

A solution of equation (1) for $f(r_o, \theta_k)$ at transducer element 10.$k$ (at $r_o, \theta_k$) due to single frequency insonification ($\omega_\alpha$) of the medium 12 by transducer 10.$j$ (at $r_o, \theta_j$) can be expressed in terms of a two dimensional integral equation involving:

(i) the complex scattering potential $S^{(\alpha)}(r,\theta)$, (ii) the position of the transducers $(r_o,\theta_j)$ and $(r_o,\theta_k)$, and (iii) tabulated Hankel (H) and Bessel (J) functions.

That solution is $$f^{(\alpha)}(r_o,\theta_k) = \sum_{m,n} \int H_m'(k_o r_o) H_n'(k_o r_o) e^{-im\theta_j - in\theta_k} J_m(k_o r) J_n(k_o r) e^{i\theta(m+n)} S^{(\alpha)}(r,\theta) r dr d\theta. \quad (2)$$

The term $f^{(\alpha)}(r_o, \theta_k)$ represents the pressure wave (frequency $\omega_\alpha$) at the position of transducer 10.$k$ expressed in terms of amplitude and phase, relative to a pressure wave originating at the position of transducer 10.$j$. This is precisely equivalent to our acquired data $m_{jk}(\omega_\alpha)$ which we described in Section B. Thus:

$$f^{(\alpha)}(r_o,\theta_k) \equiv m_{jk}(\omega_\alpha). \quad (3)$$

Therefore, we can write equation (2) as:

$$m_{jk}(\omega_\alpha) = \sum_{m,n} \int H_m'(k_o r_o) H_n'(k_o r_o) e^{-im\theta_j - in\theta_k} J_m(k_o r) J_n(k_o r) e^{i\theta(m+n)} S^{(\alpha)}(r,\theta) r dr d\theta \quad (4)$$

where:

$S^{(\alpha)}(r, \theta)$ is a complex image of medium 12 determined from data obtained at frequency $\omega_\alpha$. It is a two dimensional matrix representing the acoustic scattering potential at $(1024)^2$ $(r,\theta)$ points within a 12 mm thick slice through medium 12 in the $(r,\theta)$ plane. Each of the $(1024)^2$ complex values of $S^{(\alpha)}(r,\theta)$ includes a real and an imaginary component.

$H'_m(k_o r_o)$ is the first derivative of a Hankel function representing the antenna pattern of transmitter transducer 10.$j$ and is the correct mathematical representation for the dipole transducers used in the preferred embodiment. Hankel functions are discussed and tabulated in, for example, "The Pocketbook of Mathematical Functions," by Abramowitz and Stegun, Chapter 9, Verlag Harri Deutach 1984. The attenna pattern of any arbitrary transducer can be modeled as a weighted sum of monopole, dipole, quadrapole, etc. attenna patterns. These antenna patterns are discussed, for example, in "Classical Electrodynamics", J. D. Jackson, Chapter 16, I. Wiley and Sons, New York, 1962.

$H'_n(k_o r_o)$ is the first derivative of a Hankel function representing the antenna pattern of receiver transducer 10.$k$. For the dipole transducer used in the preferred embodiment the functions are the same as for the transmitter transducer.

$J_m(k_o r)$ and $J_n(k_o r)$ are Bessel functions determined for all values r within the $(r,\theta)$ plane based on tabulated Bessel function values.

$\mathfrak{F}$ represents the Fourier transform of the indicated functions given by $$g(\kappa,\phi) \equiv \mathfrak{F}\{f(r,\theta)\} \equiv \int\int f(r,\theta) e^{-i\kappa r \cos(\theta-\phi)} r dr d\theta \quad (5)$$

$\mathfrak{F}^{-1}$ represents the inverse Fourier transform of the indicated functions given by $$f(r,\theta) \equiv \mathfrak{F}^{-1}\{g(\kappa,\phi)\} \equiv \int g(\kappa,\phi) e^{i\kappa r \cos(\theta-\phi)} \kappa d\kappa d\theta \quad (6)$$

Equation (4) can be transformed by appropriate mathematical manipulations into the following form which gives $S^{(\alpha)}(r,\theta)$ in terms of the measured acoustic data $m_{jk}(\omega_\alpha)$.

$$S^{(\alpha)}(r,\theta) = \mathfrak{F}^{-1}\left\{\frac{1}{\mathfrak{F}\{[J_0(k_o r)]^2\}} \mathfrak{F}\left(\sum_{p,q=-512}^{512} J_p(k_o r) J_q(k_o r) e^{-i\theta(p+q)} \left[\frac{1}{H_p'(k_o r_o) H_q'(k_o r_o)}\right] \sum_{j,k=1}^{1024} m_{jk}(\omega_\alpha) e^{-ip\theta_j + iq\theta_k}\right)\right\} \quad (7)$$

D. Creating the Images

The full process of producing the $S^{(\alpha)}(r,\theta)$ image in this embodiment is described here and with reference to equation (7).

Step (1)

The first step is to calibrate the transducers. We do this by first acquiring a set of data $m_{jk}^{incident}(\omega_\alpha)$ (j,k = 1, ..., N; j$\neq$k) as described in Section B at each of 10 discrete frequencies $\omega_\alpha$($\alpha$ = 1, 2, ..., 10) with object 9 removed so that medium 12 is only the coupling fluid 11. (Frequencies are spaced at 62.5 kHz intervals between 687 kHz to 1,250 kHz.) Calibration factors are determined by asking the computer to create weighting factors to produce a uniform grey scale image when the water bath only data is processed as given by steps 2 through 9 of this Section. Addition calibration factors are determined to remove the frequency dependence of the transducers and to globally adjust each complex grey scale image of the water bath so as to provide the same image at each discrete frequency $\omega_\alpha$. These calibration factors are stored as a separate 1024 $\times$ 1024 calibration matrix for each of the 10 discrete frequencies $\omega_\alpha$($\alpha$ = 1, 2, ..., 10). These calibration matrices are stored in the memory of computer 72.

Step (2)

Data representing $m_{jk}(\omega_\alpha)$ of the medium 12 are acquired as described in Section B for each of the 10 frequencies equally spaced between 687 kHz to 1,250 kHz. For each frequency $\omega_\alpha$, $m_{jk}(\omega_\alpha)$ is an 1024 $\times$ 1024 complex matrix of phase and amplitude data.

Step (3)

For each discrete frequency $\omega_\alpha$, computer 72 multiplies the $m_{jk}(\omega_\alpha)$ data by the calibration matrix determined in Step (1) of this Section to provide calibrated $m_{jk}(\omega_\alpha)$ data.

Step (4)

Using the calibrated $m_{jk}(\omega_\alpha)$ data, computer 72 calculates the quantity $$\sum_{j,k=1}^{1024} m_{jk}(\omega_\alpha) e^{-ip\theta j + iq\theta k} \tag{8}$$

for each frequency $\omega_\alpha$. This manipulation constitutes a fast Fourier transform of the calibrated complex matrix $m_{jk}(\omega_\alpha)$. The result of this transformation is that the calibrated $m_{jk}(\omega_\alpha)$ data for each frequency $\omega_\alpha$ is now in the form of a $1024 \times 1024$ matrix in an azimuthal mode space dependent on azimuthal mode values designated by the azimuthal mode numbers p and q.

Step (5)

We now calculate the antenna patterns $H'_p(k_o r_o)$ and $H'_q(k_o r_o)$ for each of the transducers 10. This involves tabulation of the first derivatives of Hankel functions for azimuthal mode numbers p,q = −512 to 512. These values are stored in the memory of computer 72.

Step (6)

In this step we simply divide the quantity determined in Step (4) by the product of the antenna patterns calculated in Step (5) for each transmitter-receiver combination at frequency $\omega_\alpha$ and each mode combination (p,q) to calculate the following quantity:

$$\frac{\sum_{j,k=1}^{1024} m_{jk}(\omega_\alpha) e^{ip\theta j + iq\theta k}}{H_p'(k_o r_o) H_q'(k_o r_o)} \tag{9}$$

Step (7)

We now calculate a weighting function $J_p(k_o r) J_q(k_o r) e^{-i\theta(p+q)}$ at each point r and $\theta$ which is a $1024 \times 1024$ dimensional matrix. $J_p$ and $J_q$ are determined from a Bessel function table stored in the memory of computer 72.

Step (8)

Next we multiply the quantity calculated in Step (6) by the weighting function calculated in Step (7) and sum over azimuthal modes p and q to obtain the quantity:

$$S^{(\alpha)}_{conv}(r,\theta) = \tag{10}$$

$$\sum_{p,q=-512}^{512} J_p(k_o r) J_q(k_o r) e^{-i\theta(p+q)} \left[ \frac{\sum_{j,k=1}^{1024} m_{jk}(\omega_\alpha) e^{ip\theta + iq\theta}}{H_p'(k_o r) H_q'(k_o r)} \right]$$

This step is done at each point (r,$\theta$) in the medium 12. The result of this step is $S^{(\alpha)}_{conv}(r,\theta)$. This is an image of $S^{(\alpha)}(r,\theta)$ but it is convolved with $[J_o(k_o r)]^2$ which presents a smoothed image of $S^{(\alpha)}(r,\theta)$. For a more accurate image we need to deconvolve the quantity $[J_o(k_o r)]^2$ from $S^{(\alpha)}_{conv}(r,\theta)$.

Step (9)

Convolution and deconvolution methods are standard mathematical calculations and are discussed, for example, in "Discrete-Time Signal Processing", pg. 58, by Oppenheim and Schafer, Prentice-Hall (1989). Convolutions and deconvolutions of two spatial functions can be calculated in the spatial domain or in the Fourier wavevector domain. The preferred embodiment calculates the convolutions and deconvolutions in the Fourier wavevector domain. However, persons skilled in the art will recognize that these convolutions and deconvolutions can easily be done in the spatial domain. The Fourier transform of $$[J_o(k_o r)]^2 \text{ is } \frac{1}{\pi} \frac{1}{\kappa} \frac{1}{(4k_o - \kappa)^{\frac{1}{2}}}.$$

Thus we deconvolve $[J_o(k_o r)]^2$ from $S_{conv}^{(\alpha)}(r,\theta)$ to calculate an image $S^{(\alpha)}(r,\theta)$ as follows:

$$S^{(\alpha)}(r,\theta) = \mathfrak{I}^{-1}\{\pi\kappa(4k_o - \kappa)^{\frac{1}{2}} \mathfrak{I}\{S_{conv}^{(\alpha)}(r,\theta)\}\}. \tag{11}$$

Using equation (11) we can produce an image $S^{(\alpha)}(r,\theta)$ at each frequency $\omega_\alpha$ of medium 12: To show the images on a digital computer monitor, computer 72 is programmed to convert from polar coordinates (r,$\theta$) to cartesian coordinates (x,y) to produce $S^{(\alpha)}(x,y)$. Each of the $S^{(\alpha)}(x,y)$ is a matrix of values. Each value of the matrix contains two numbers, a first number representing a real part of the value and a second number representing an imaginary part of the value.

The magnitude of these numbers can be represented as a grey scale on a computer monitor at a grid pixel (x,y). (The larger the number the whiter the pixel or vise versa.) When this is done we get two separate images for each frequency, one from the real part of the value of S and one from the imaginary part of S.

E. Combining the Single Frequency Images

As stated above the values of $S^{(\alpha)}(r,\theta)$ at discrete frequencies $\omega_\alpha$ produce good images of medium 12. Over a certain frequency range such as 687 kHz to 1.25 MHz, for example, in which the sound speed and attenuation coefficient of the medium 12 are approximately frequency independent, the images of $S^{(\alpha)}(r,\theta)$ acquired at different frequencies $\omega_\alpha$ ideally would present the same images of the medium 12, independent of frequency $\omega_\alpha$. However, the images can be complicated by frequency dependent artifacts resulting from reflections of acoustic energy from the faces of the receiver transducers 10.k and from multiple scattering events within the medium 12. We have found that combining images of $S^{(\alpha)}(r,\theta)$ reconstructed at different frequencies $\omega_\alpha$ reduces the image artifacts and improves the image quality. The following discussion centers on seven preferred ways of combining single frequency images $S^{(\alpha)}(r,\theta)$ reconstructed at different frequencies $\omega_\alpha$.

For the purposes of combining images $S^{(\alpha)}(r,\theta)$ formed at different frequencies $\omega_\alpha$, we have found it useful to define a term $\hat{S}^{(\alpha)}(r,\theta)$ which we calculate as:

$$\hat{S}^{(\alpha)}(r,\theta) = \mathfrak{I}^{-1}\{\kappa^{-1} \mathfrak{I}\{S^{(\alpha)}(r,\theta)\}\}. \tag{12}$$

In equation (12), $\hat{S}^{(\alpha)}(r,\theta)$ is calculated by first calculating an FFT of $S^{(\alpha)}(r,\theta)$, then dividing by $\kappa$ and calculating the inverse FFT of the result.

1) Sum of the complex images $S^{(\alpha)}(r,\theta)$.

From the acquired data $m_{jk}(\omega_\alpha)$, we reconstruct separate images of $S^{(\alpha)}(r,\theta)$ at each frequency $\omega_\alpha$ ($\alpha=1,2,\ldots,10$) as given in Steps (1)–(9) of Section D. We then sum these complex images to produce:

$$S_{total}(r,\theta) = \sum_{\alpha=1}^{10} S^{(\alpha)}(r,\theta). \tag{13}$$

We convert to cartesian coordinates (x,y) to produce an image $S_{total}(r,\theta)$ which has less artifact and more clarity than each single frequency image $S^{(\alpha)}(r,\theta)$.

2) Sum of magnitudes of $S^{(\alpha)}(r,\theta)$ Images

From the acquired data $m_{jk}$ ($\omega_\alpha$), we reconstruct separate images of $S^{(\alpha)}(r,\theta)$ at each frequency $\omega_\alpha$ ($\alpha=1,2,\ldots,10$) as given in Steps (1)–(9) of Section D. We then calculate the magnitudes of these complex images as $|S^{(\alpha)}(r,\theta)| = [S^{(\alpha)}(r,\theta)S^{(\alpha)*}(r,\theta)]^{\frac{1}{2}}$ where $S^{(\alpha)*}(r,\theta)$ is the complex conjugate of $S^{(\alpha)}(r,\theta)$. We then sum the magnitudes of these images to produce:

$$|S_{total}(r,\theta)| = \sum_{\alpha=1}^{10} |S^{(\alpha)}(r,\theta)|. \qquad (14)$$

Again we convert to cartesian coordinates to produce an image $|S_{total}(r,\theta)|$ which has less artifacts and more clarity than each image $|S^{(\alpha)}(r,\theta)|$.

3) Sound Speed and Attenuation Maps Calculated from $S^{(\alpha)}(r,\theta)$ Images Sound speed maps and attentuation maps of medium 12 can be calculated from $S^{(\alpha)}(r,\theta)$ as follows:

Step (1)

From the acquired data $m_{jk}$ ($\omega_\alpha$), we reconstruct separate images of $S^{(\alpha)}(r,\theta)$ at each frequency $\omega_\alpha$ ($\alpha=1,2,\ldots,10$) as given in Steps (1)–(9) of Section D. We then calculate the maps $\hat{S}^{(\alpha)}(r,\theta)$ at each frequency $\omega_\alpha$ as given in equation (12).

Step (2)

Computer 72 then calculates the following function $$P(r,\theta,\tau) = \left| \sum_{\alpha=1}^{10} e^{i\omega_\alpha \tau} \hat{S}^{(\alpha)}(r,\theta) \right|^2 \qquad (15)$$

For each point $(r,\theta)$ in the medium 12, $P(r,\theta,\tau)$ represents a synthesized acoustic pulse $P(\tau)$ focused at the point $(r,\theta)$.

Step (3)

For each point $(r,\theta)$ in the medium 12, $P(\tau)$ has a maximum value $P_{max}$ at a value of $\tau$ which we call $\tau_{max}$. The computer 72 is programmed to find, for each point $(r,\theta)$, $P_{max}(r,\theta)$ and to determine the value of $\tau_{max}(r,\theta)$.

Step (4)

The computer 72 then creates a sound speed map $c(r,\theta)$ of medium 12 by the following calculation $$c(r,\theta) = \mathfrak{I}^{-1}\{\kappa \mathfrak{I}\{2r_o/\tau_{max}(r,\theta)\}\} + c_o. \qquad (16)$$

In equation (16), $r_o$ is the radius of the transducer ring and $c_o$ is the sound speed of the coupling fluid 11.

Step (5)

The computer then creates an attenuation map $N(r,\theta)$ of medium 12 by the following calculation $$\mu(r,\theta) = \mathfrak{I}^{-1}\left\{\kappa \mathfrak{I}\left\{\frac{1}{2r_o} \ln P_{max}(r,\theta)\right\}\right\} + \mu_o \qquad (17)$$

In equation (17), $\mu_o$ is the attenuation coefficient of the coupling fluid 11. These values of $c(r,\theta)$ and $N(r,\theta)$ are $1024 \times 1024$ matrixes in r and $\theta$. They are converted to cartesian coordinates (x,y) and displayed on a computer screen with the values of c and N depicted as gray scale values.

4) Refined Sound Speed and Attenuation Maps Calculated from $S^{(\alpha)}(r,\theta)$ The sound speed $c(r,\theta)$ and attenuation $N(r,\theta)$ maps calculated in equations (15)–(17) represent approximate images of the medium 12. This section discusses refined calculations of $c(r,\theta)$ and $N(r,\theta)$ from the single frequency images $S^{(\alpha)}(r,\theta)$ which represent more accurate images of the medium 12.

Step (1)

From the acquired data $m_{jk}$ ($\omega_\alpha$), we reconstruct separate images of $S^{(\alpha)}(r,\theta)$ at each frequency $\omega_\alpha$ ($\alpha=1,2,\ldots,10$) as given in Steps (1)–(9) of Section D. We then calculate the maps $\hat{S}^{(\alpha)}(r,\theta)$ at each frequency $\omega_\alpha$ as given in equation (12).

Step (2)

We then calculate the maps $\hat{S}_{\Delta p,\Delta q}^{(\alpha)}(r,\theta)$ at each frequency $\omega_\alpha$ ($\alpha=1,2,\ldots,10$) as such:

$$\hat{S}_{\Delta p,\Delta q}^{(\alpha)}(r,\theta) = \mathfrak{I}^{-1}\left\{ e^{i(\Delta p+\Delta q)(\theta k+\frac{\pi}{2})} \cos\left[(\Delta p - \Delta q)\cos^{-1}\left(\frac{\kappa}{2k_o}\right)\right] \cdot \mathfrak{I}\{\hat{S}^{(\alpha)}(r,\theta)\} \right\} \qquad (18)$$

The maps $\hat{S}_{\Delta p,\Delta q}^{(\alpha)}(r,\theta)$ represent coupling of acoustic energy from azimuthal modes p and q to modes $p+\Delta p$ and $q+!q$.

Step (3)

Computer 72 then calculates the following function:

$$P_{corr}(r,\theta,\tau) = \sum_{\Delta p, \Delta q} \left| \sum_{\alpha=1}^{10} e^{i\omega_\alpha \tau} \hat{S}_{\Delta p,\Delta q}^{(\alpha)}(r,\theta) \right|^2. \qquad (19)$$

We have had excellent results using sums of $!p = -6$ to $+6$, $!q=0$; $!p=0$, $!q=-6$ to $+6$; and $!p=-6$ to $+6$, $!q=-6$ to $+6$. Other combinations of !p and !q could be used.

For each point $(r,\theta)$ in the medium 12, $P_{corr}(r,\theta,\tau)$ represents a synthesized acoustic pulse $P_{corr}(\tau)$ focused at the point $(r,\theta)$. $P_{corr}(r,\theta,\tau)$ is a refined version of the function $P(r,\theta,\tau)$ given in equation (15).

Step (4)

For each point $(r,\theta)$ in the medium 12, $P_{corr}(\tau)$ has a maximum value $P_{max}$ at a value of $\tau$ which we call $\tau_{max}$. The computer 72 is programmed to find, for each point $(r,\theta)$, $P_{max}(r,\theta)$ and to determine the value of $\tau_{max}(r,\theta)$ as was done in Step (3) of Section E.3 except we use $P_{corr}(r,\theta,\tau)$ instead of $P(r,\theta,\tau)$).

Step (5)

Using the refined values of $\tau_{max}(r,\theta)$ and $P_{max}(r,\theta)$, we now calculate the sound speed $c(r,\theta)$) and attenuation $N(r,\theta)$ maps as we did in equations (16) and (17).

5) Sum of Phase Aberration Corrected $S^{(\alpha)}(r,\theta)$ Images

The complex images $S^{(\alpha)}(r,\theta)$ reconstructed as given in Steps (1)–(9) of Section F represent approximate images of the medium 12. The complex phase of these images can be distorted at each point $(r,\theta)$ due to limitations of the reconstruction algorithm as given in Steps (1)–(9) of Section D. This Section discusses a correction method for the phase aberrations in the images $S^{(\alpha)}(r,\theta)$ and the combination of these images to reduce image artifacts.

Step (1)

From the acquired data $m_{jk}$ ($\omega_\alpha$), we reconstruct separate images of $S^{(\alpha)}(r,\theta)$ at each frequency $\omega_\alpha$ ($\alpha=1,2,\ldots,10$) as given in steps (1)–(9) of Section D.

We then calculate the maps $\hat{S}^{(\alpha)}(r,\theta)$ at each frequency $\omega_\alpha$ as given equation (12).

Step (2)

We calculate the map $\tau_{max}(r,\theta)$ as described by the procedures given in Section E.3 or section E.4.

Step (3)

Computer 72 calculates the map $\hat{S}_{total}(r,\theta)$ as such:

$$\hat{S}_{total}(r,\theta) = \sum_{\alpha=1}^{10} e^{i\omega_\alpha \tau_{max}(r,\theta)} \hat{S}^{(\alpha)}(r,\theta) \quad (20)$$

Step (4)

The final image $S_{total}(r,\theta)$ is determined by the following calculation:

$$S_{total}(r,\theta) = \mathfrak{I}^{-1}\{\kappa \mathfrak{I}\{\hat{S}_{total}(r,\theta)\}\} \quad (21)$$

This image displays only high spatial frequency components (i.e., fine details) of medium 12. These fine details include sharp edges or discontinuities in the sound speed in the medium 12 and also small objects with a scale size comparable to the acoustic wavelengths.

6) Composite Image

The image $S_{total}(r,\theta)$ calculated in Section E.5 can be combined with the map $\tau_{max}(r,\theta)$ to provide a composite map $S_{comp}(r,\theta)$ which is a more accurate representation of the medium 12. The $S_{comp}(r,\theta)$ image contains both the high spatial frequency components and low spatial frequency components of the medium 12.

Step (1)

The computer 72 calculates $\tau_{max}(r,\theta)$ as described by the procedures given in Section E.3 or E.4 and $\hat{S}_{total}(r,\theta)$ given by equation (20).

Step (2)

Computer 72 then calculates:

$$\hat{S}_{comp}(r,\theta) = \frac{1}{i\Delta\omega}[\ln\hat{S}_{total}(r,\theta)] + \tau_{max}(r,\theta) \quad (22)$$

In equation (22), In denotes the natural logarithm and $\Delta\omega$ is the spacing between frequencies $\omega_\alpha$ ($\Delta\omega = 62.5$ kHz in the preferred embodiment).

Step (3)

Computer 72 then calculates $S_{comp}$ as follows:

$$S_{comp}(r,\theta) = \mathfrak{I}^{-1}\{\kappa \mathfrak{I}\{\hat{S}_{comp}(r,\theta)\}\}. \quad (23)$$

Computer 72 then converts $S_{comp}(r,\theta)$ to cartesian coordinates (x,y) and displays on computer monitor.

7) Further Refined Sound Speed Map Calculated from $\hat{S}^{(\alpha)}(r,\theta)$ This section discusses a method to further refine the accuracy of the sound speed maps $c(r,\theta)$ calculated in Sections E.3 and E.4. In Sections E.3 and E.4 we calculate at each point $(r,\theta)$ the transit time $\tau_{max}(r,\theta)$ as the value $\tau$ in which the pulse $P(\tau)$ has a maximum value $P_{max}$ and derive sound speed maps from this information. In this Section, we calculate the transit time $\tau_{av}(r,\theta)$ as the averaged arrival time of the power contained in the pulse $P(\tau)$. This map $\tau_{ax}(r,\theta)$ is then used to calculate refined maps of the sound speed $c(r,\theta)$ of the medium 12.

Step (1)

Computer 72 computes the following quantity:

$$P_{av}(r,\theta) = \sum_{\Delta p, \Delta q} \sum_{\alpha=1}^{9} [\hat{S}^{(\alpha)}_{\Delta p, \Delta q}(r,\theta)][\hat{S}^{(\alpha+1)}_{\Delta p, \Delta q}(r,\theta)]^* \quad (24)$$

where $\hat{S}_{\Delta p,\Delta q}{}^{(\alpha)}(r,\theta)$ is calculated as in equation (18) and * denotes the complex conjugate. The preferred embodiment includes sums of 1) !p=−6 to +6; !q=0; 2) !p=0, !q=−6+6; or 3) !p=−6+6, !q=−6 to +6. Other combinations of $\Delta p$ and $\Delta q$ could be used.

Step (2)

The computer 72 calculates an average transit time $\tau_{ax}(r,\theta)$ image of medium 12 by the following calculation $$\tau_{av}(r,\theta) = \frac{i}{2\Delta\omega} \ln P_{av}(r,\theta) \quad (25)$$

Step (3)

The computer 72 then calculates a sound speed image $c(r,\theta)$ of medium 12 by the following calculation $$c(r,\theta) = \mathfrak{I}^{-1}\{\kappa \mathfrak{I}\{2r_o/\tau_{av}(r,\theta)\}\} + c_o. \quad (26)$$

Step (4)

The computer 72 then creates an attenuation image $\mu(r,\theta)$ of medium 12 by the following calculation $$\mu(r,\theta) = \mathfrak{I}^{-1}\left\{\kappa \mathfrak{I}\left\{\frac{1}{2r_o}\ln P_{av}(r,\theta)\right\}\right\} \quad (27)$$

F. Computer Simulations

Figure 3:
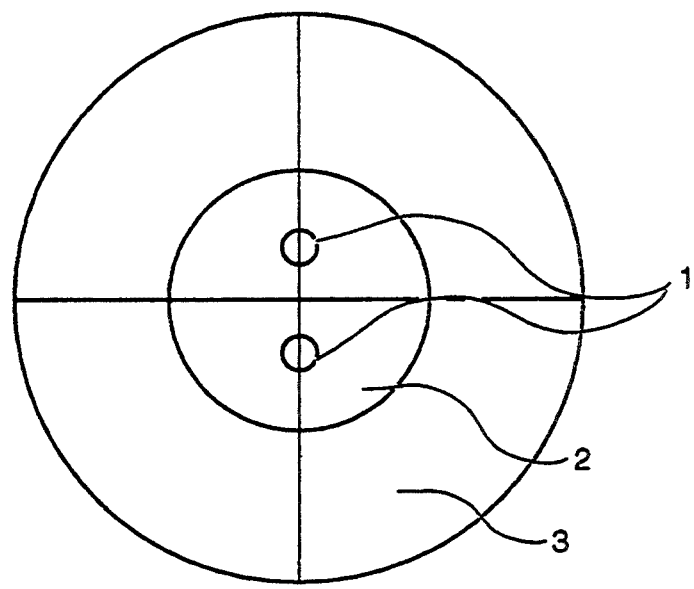
FIG. 3 is a diagram of the computer simulated object used to demonstrate some of the features of the present invention.
Figure 4:
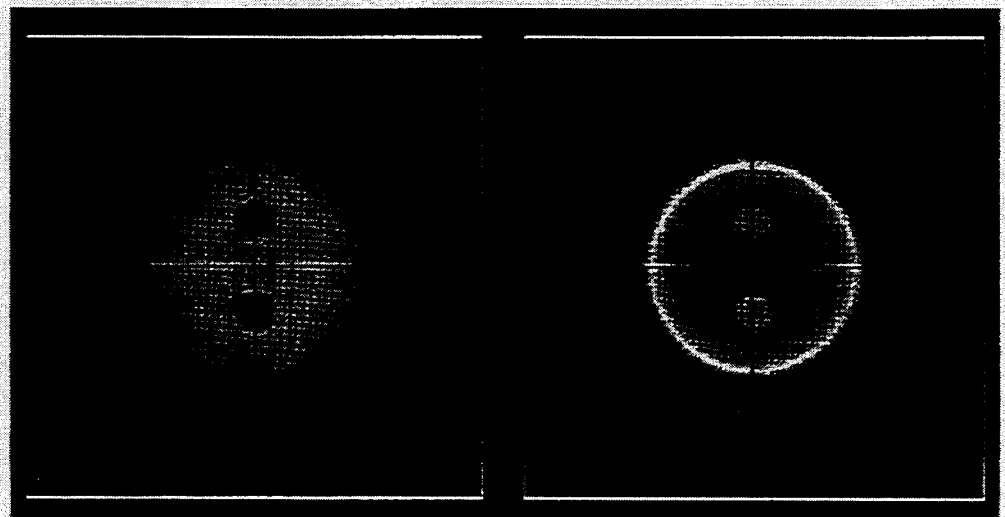
FIG. 4 are the real (right) and imaginary (left) components of a single frequency image of the simulated object.
Figure 5:
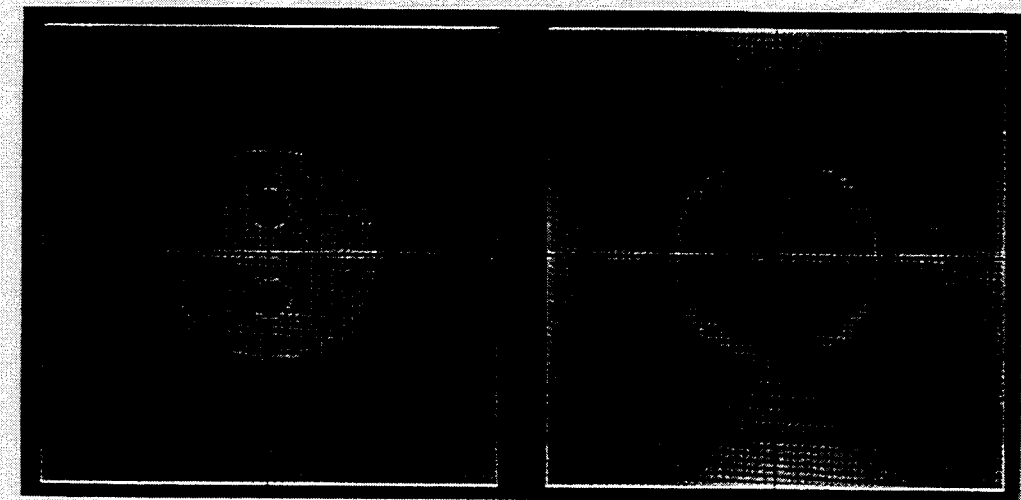
FIG. 5 are sound speed $c(r,\theta)$ (left) and attenuation $\mu(r,\theta)$ (right) maps of the simulated object.
Figure 6:
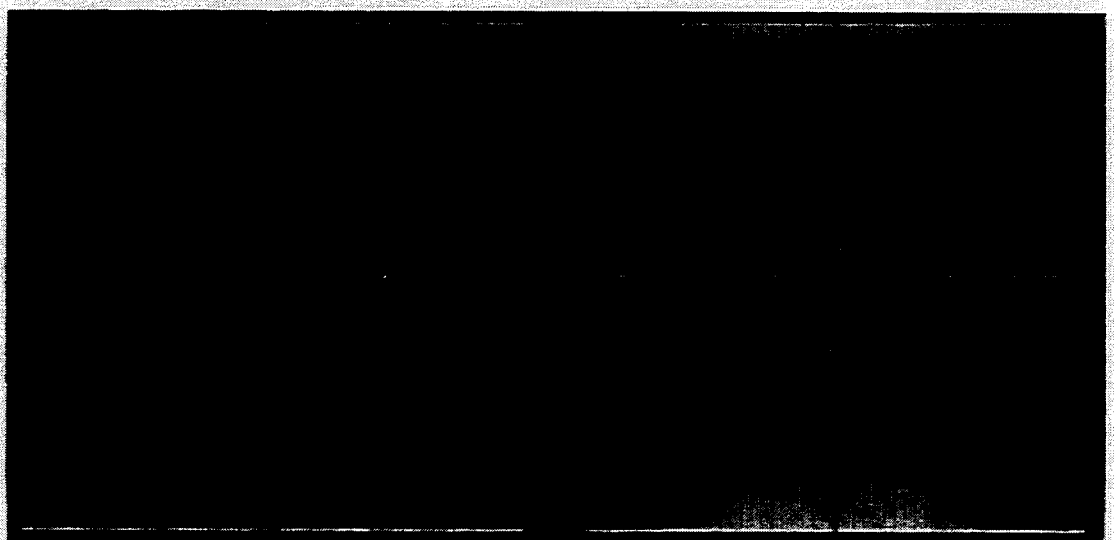
FIG. 6 are the real (right) and imaginary (left) components of the simulated object. The images are the summation of single frequency images as described in FIG. 5 which have been phase aberration corrected.
Figure 7:
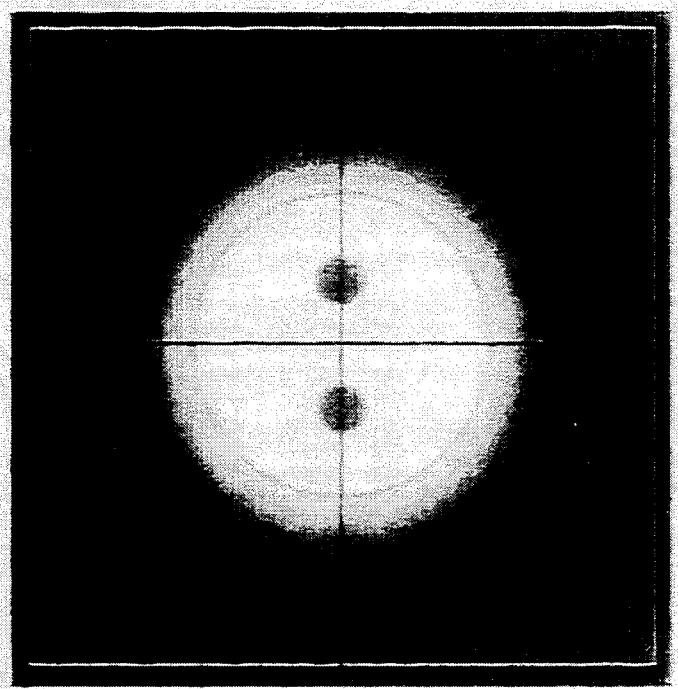
FIG. 7 is a composite image of a simulated object. This composite image combines the sound speed map described in FIG. 6 with real component of the image described in FIG. 7.

We created computer simulations in order to check our algorithms. No hardware other than a computer was used in these reconstructions. FIGS. 4–7 display images reconstructed from simulated data at 1 MHz, using the same transducer configuration as our working prototype system. The simulated object shown in FIG. 3 is a 3-inch diameter cylinder 2 of a homogeneous material having a sound speed which is 5% greater than the surrounding coupling fluid. The two 1 cm diameter voids 1 in the object have the same sound speed as the coupling fluid 3 surrounding the object. The attenuation coefficients of the object and the coupling fluid are equal to zero (no attenuation). The images were produced by the following methods: FIG. 4 displays the real (right) and imaginary (left) components of a single frequency reconstruction as described in Section D. FIG. 5 displays the sound speed and attenuation images as described in Section E.4. FIG. 6 displays the real (right) and imaginary (left) components of a ten single frequency reconstructions which have been corrected for phase aberrations and summed as described in Section E.5. FIG. 6 displays a composite image as described in Section E.6.

G. Actual Images

Figure 8:
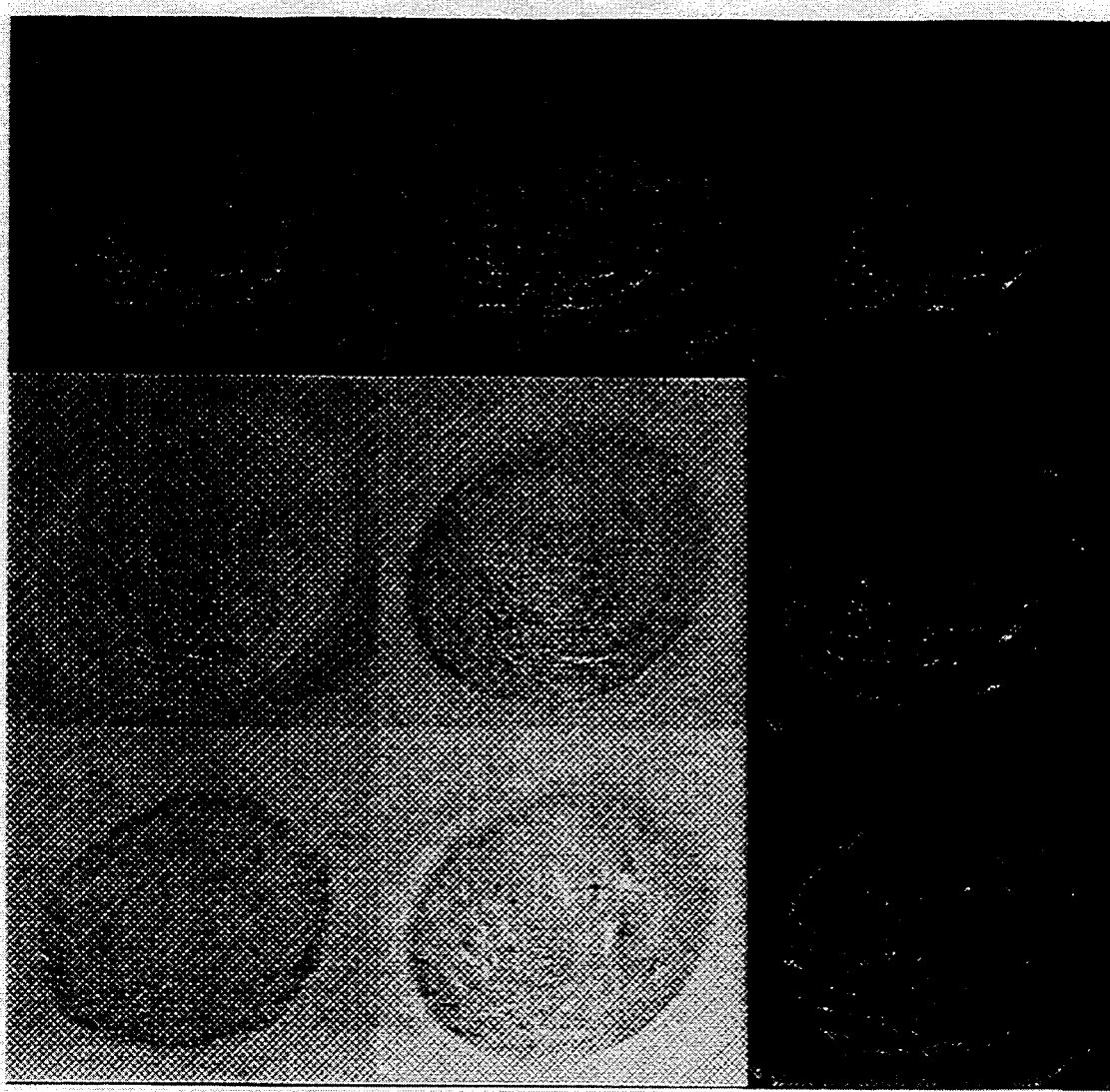
FIG. 8 displays nine images of a female breast produced with the preferred algorithms using the prototype device described in FIGS. 1–3.
Figure 9:
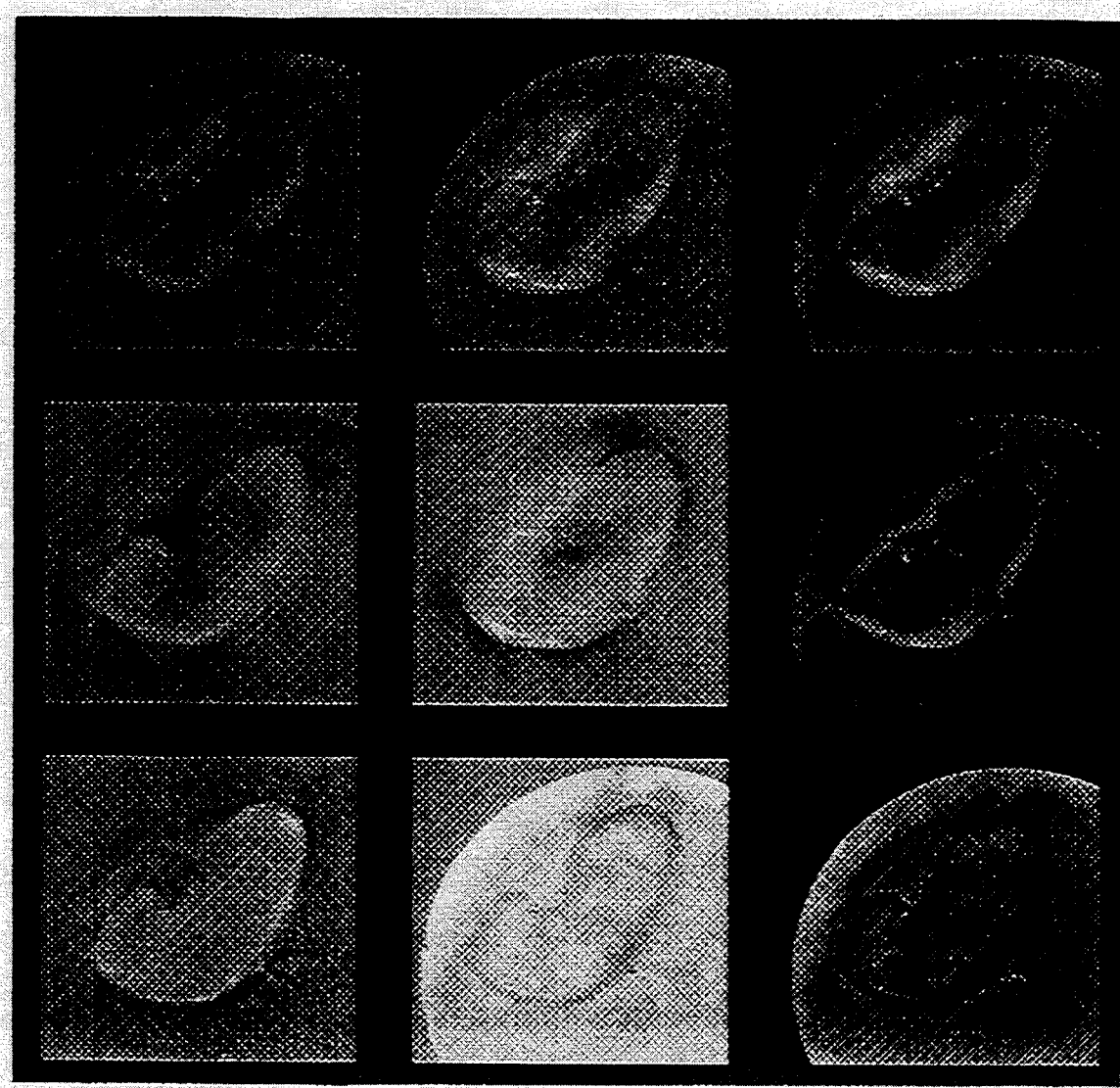
FIG. 9 displays nine images of a porcine kidney produced with the preferred algorithms using the prototype device described in FIGS. 1–3.

FIGS. 8–12 display actual images obtained using the prototype device described in Sections A–D. FIG. 8 displays nine images of a 1.2 cm slice of a female breast. The acquired data is the same for all nine images, the reconstruction methods are different for each image. Beginning from the top left corner and progressing left to right the images are 1) real component of single frequency image (Section D), 2) imaginary component of a single frequency image (Section D), 3) magnitude of five single frequency images which have been summed (Section E.1), 4) real component of single frequency image which has been corrected for phase aberrations (Section E.5), 5) imaginary component of single frequency image which has been corrected for phase aberrations (Section E.5), 6) magnitude of five single frequency images each which has been corrected for phase aberrations (Section E.5), 7) sound speed image (Section E.7), 8) attenuation image (Section E.7), and 9) square root of sum of squares of sound speed and attenuation images (Section E.7). FIG. 9 displays nine images of an excised porcine kidney obtained using the prototype device described in Sections A–B and reconstructed with the methods described for FIG. 8.

Figure 10:
FIG. 10 displays images of nine slices of a normal female breast produced with the prototype device described in FIGS. 1–3.
Figure 11:
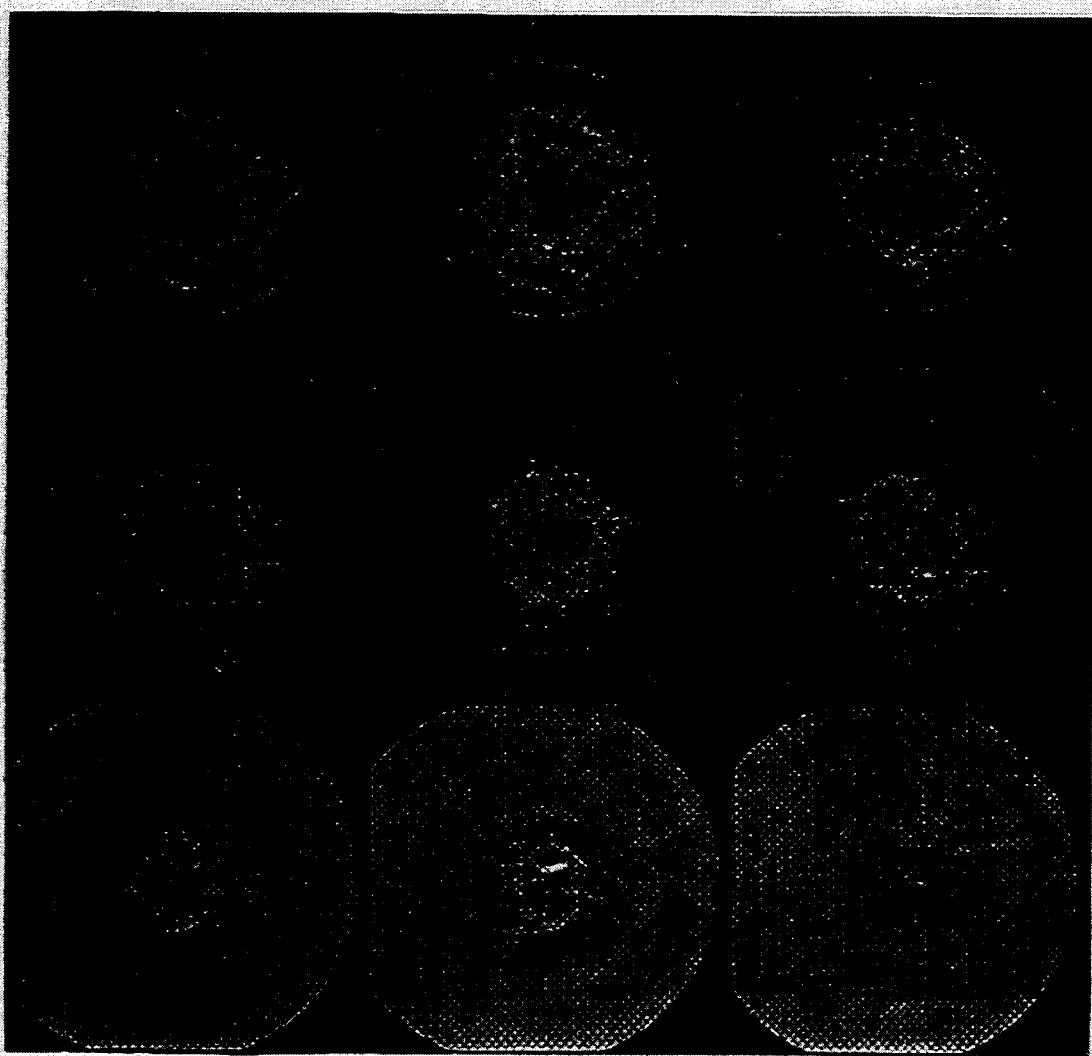
FIG. 11 displays images of nine slices of a cystic female breast produced with the prototype device described in FIGS. 1–3.
Figure 12:
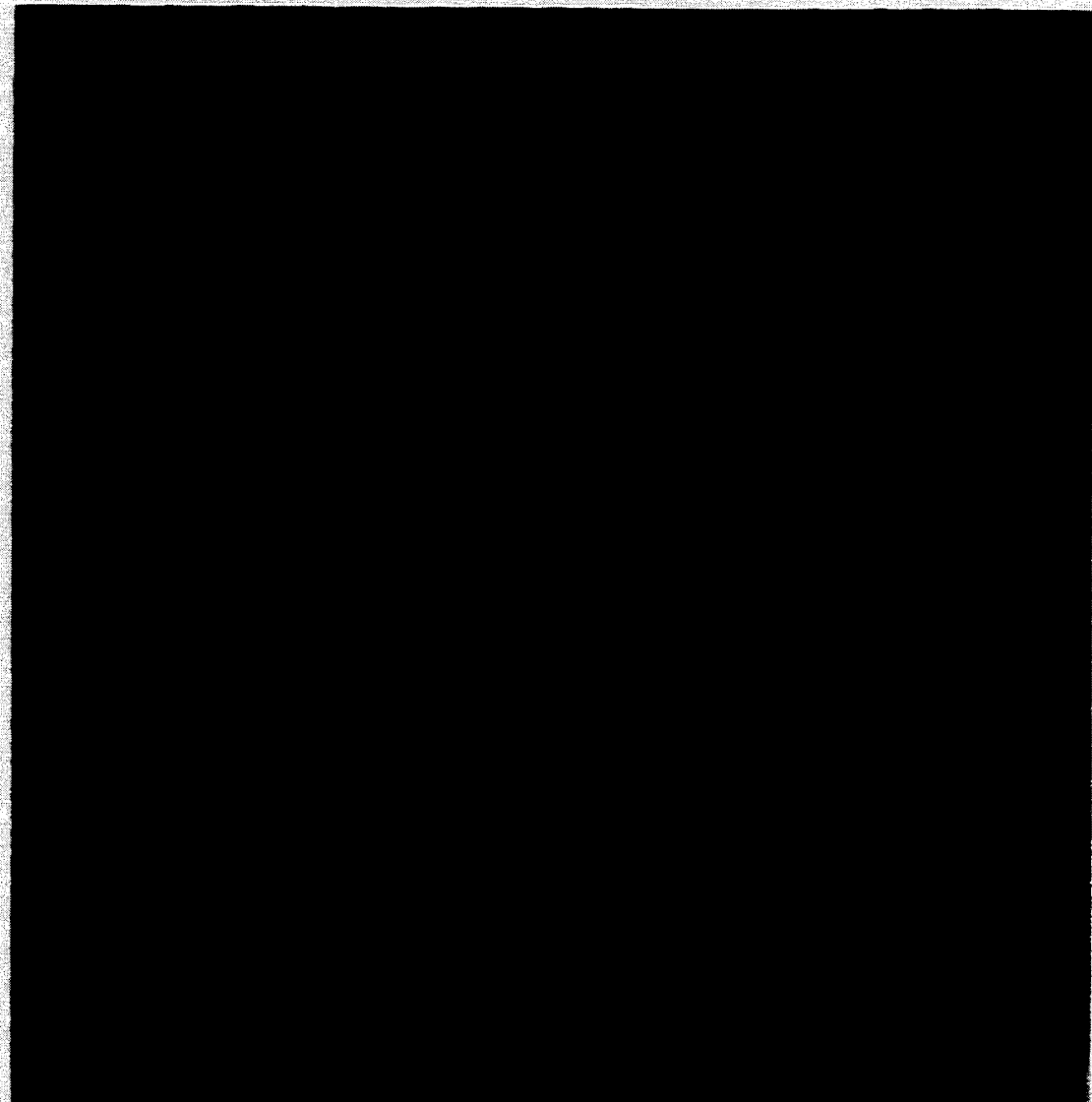
FIG. 12 displays an image of a porcine kidney produced with the prototype device described in FIGS. 1–3.

FIG. 10 displays nine images of a female breast obtained with the prototype device described in Sections A–B and with reference to FIG. 12. The female lays prone face down on a table and positioned her left breast through an eight inch hole into a water bath containing the transducer assembly 80. Beginning at the top left corner of FIG. 10, the nine images were obtained by sequentially moving the transducer assembly 80 from the area of the female breast 86 close to the chest wall to the nipple of the breast in 1 centimeter steps. The images are each magnitudes of the sum of five single frequency images each which has been corrected for phase aberrations as described in Section E.5. FIG. 11 displays similar images for another female breast in which ther is a large fluid filled cyst.

FIG. 12 displays an image of an excised porcine kidney obtained using the prototype device described in Sections A–B and reconstructed with the method described in Section E.5.

H. Biopsy Needle Guidance

Figure 15:
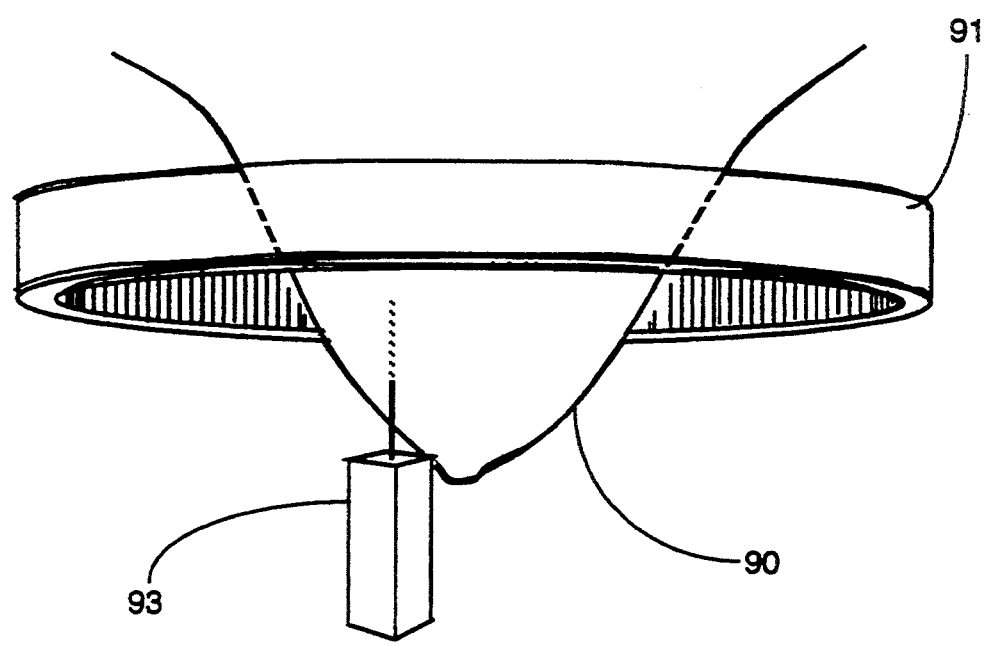
FIG. 15 is an illustration of an application of the invention utilized for biopsy needle guidance.

The invention can be used for the monitoring of a biopsy needle as it is inserted in a volume of human tissue such as, for example, the female breast. FIG. 15 displays an illustration of the invention for this purpose. The coupling of the acoustic energy from the transducer ring 91 to the breast 90 may be accomplished with the use of a fluid filled bladder which conforms to the breast. Tomographic images of several slices of the breast are produced as in FIG. 10 to locate the biopsy location. The volume of the breast to be biopsied is determined from these tomographic images. A computer analyses the tomographic image and determines where tip of the biopsy needle 93 is to be placed. The computer then guides the biopsy needle tip to the predetermined location. A second set of tomographic images are obtained with the biopsy needle in place to verify the position of the needle tip.

I. Images of Temperature Distributions

This invention provides a device and a method for measuring variations in temperature of the medium 12. This is accomplished by virtue of the fact that temperature changes in human tissue result in changes in the sound speed of the tissue. The sound speed of human tissue which has been locally heated can be expressed as $$c(r,\theta)\{\text{heated}\} = c(r,\theta) + \Delta T(r,\theta)[d/dT\ c(r,\theta)] \quad (26)$$

where $\Delta T(r,\theta)$ is the temperature distribution resulting from local heating of the tissue, $c(r,\theta)$ is the sound speed map of the tissue at the ambient body temperature, and $d/dT\ c(r,\theta)$ is the differential change in sound speed with respect to temperature. For example, in human liver tissue at 37° C., $c(r,\theta) = 1596$ m/sec and $d/dT\ c(r,\theta) = 0.96$ m/(sec−°C.). A $\Delta T = 5°$ C. change in temperature due to local heating of the liver by laser or microwave heating would produce a change in sound speed of $[c(r,\theta)^{-1}]\Delta T(r,\theta)\ [d/dT\ c(r,\theta)] = 0.3\%$.

The invention can be used to produce a combination sound speed and temperature image by locally heating a volume of the tissue and then by directly imaging the sound speed of the tissue as prescribed in the procedures given in Sections A–F. Alternatively, one can produce a sound speed image of the tissue before and after locally heating a volume of the tissue and then subtracting or dividing the two images to produce an image of the temperature distribution.

J. Alternate Embodiments

An alternate embodiment involves the use of a periodic wideband insonification signal in which a periodic time-varying signal is transmitted into the medium sequentially from each transducer. The signal has a 1 MHz center frequency, a 600 kHz frequency bandwidth, and repeats every 16 microseconds. The Fourier transform of this signal is a comb of ten discrete frequencies evenly spaced in 62.5 kHz intervals from 687 KHz to 1.25 MHz. The relative acoustic signal strengths of the discrete frequency components is fairly uniform across the frequency range. The relative phases of the discrete frequency components are randomized in order to provide a fairly flat temporal response of the periodic time-varying signal. The wideband signal reaches a steady state condition after approximately 270 microseconds which is twice the acoustic travel time across the diameter of the transducer ring. After this time, each receiver sees a time varying signal that repeats every 16 microseconds. Data is acquired and stored from each receiver for 16 microseconds at a 4 MHz data rate. The acquisition method is repeated with each transducer acting as a transmitter of sound. A Fourier transform of the time-varying receiver signals provides multi-frequency data with a frequency resolution of 62.5 kHz (1/(16 microseconds)). The data set is comparable to the data taken by the acquisition method described in Sections C and D in which 10 separate data sets are acquired at ten discrete frequencies spaced 62.5 kHz apart from 650 kHz to 1.25 MHz. However, the total acquisition time is reduced to 3 seconds with the wideband acquisition method.

Figure 13:
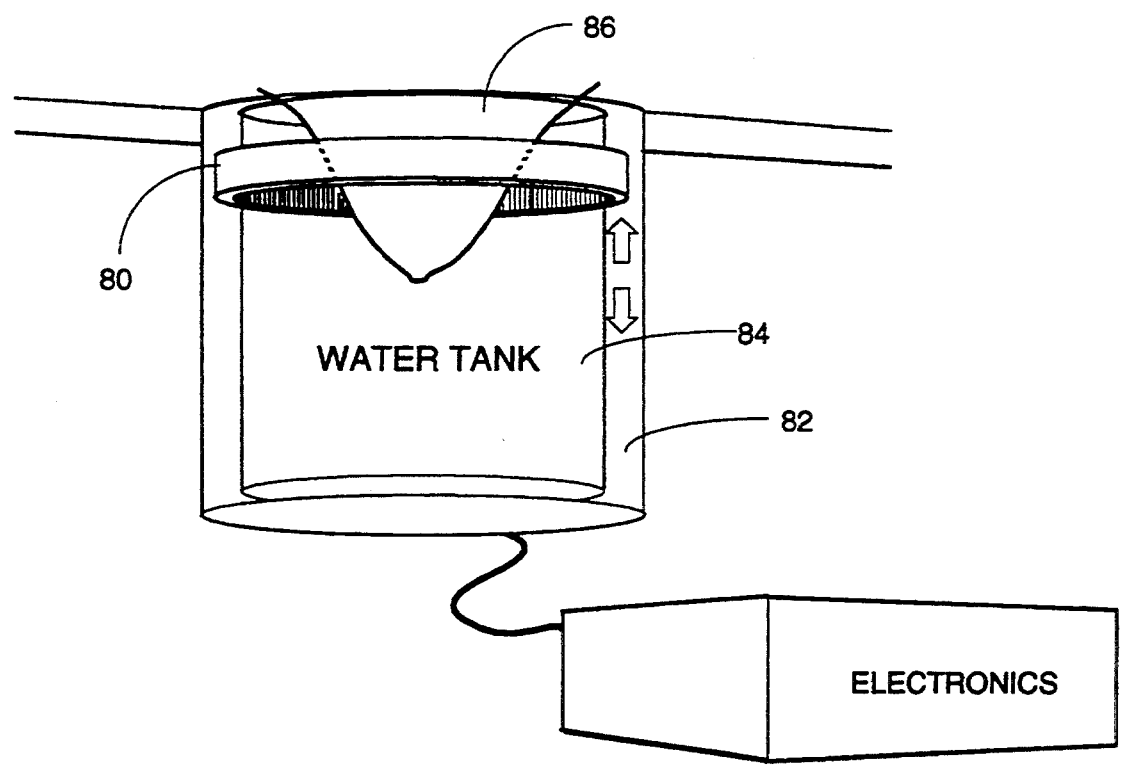
FIG. 13 is an illustration of the invention utilized for breast imaging showing how slices at various locations are obtained.
Figure 14:
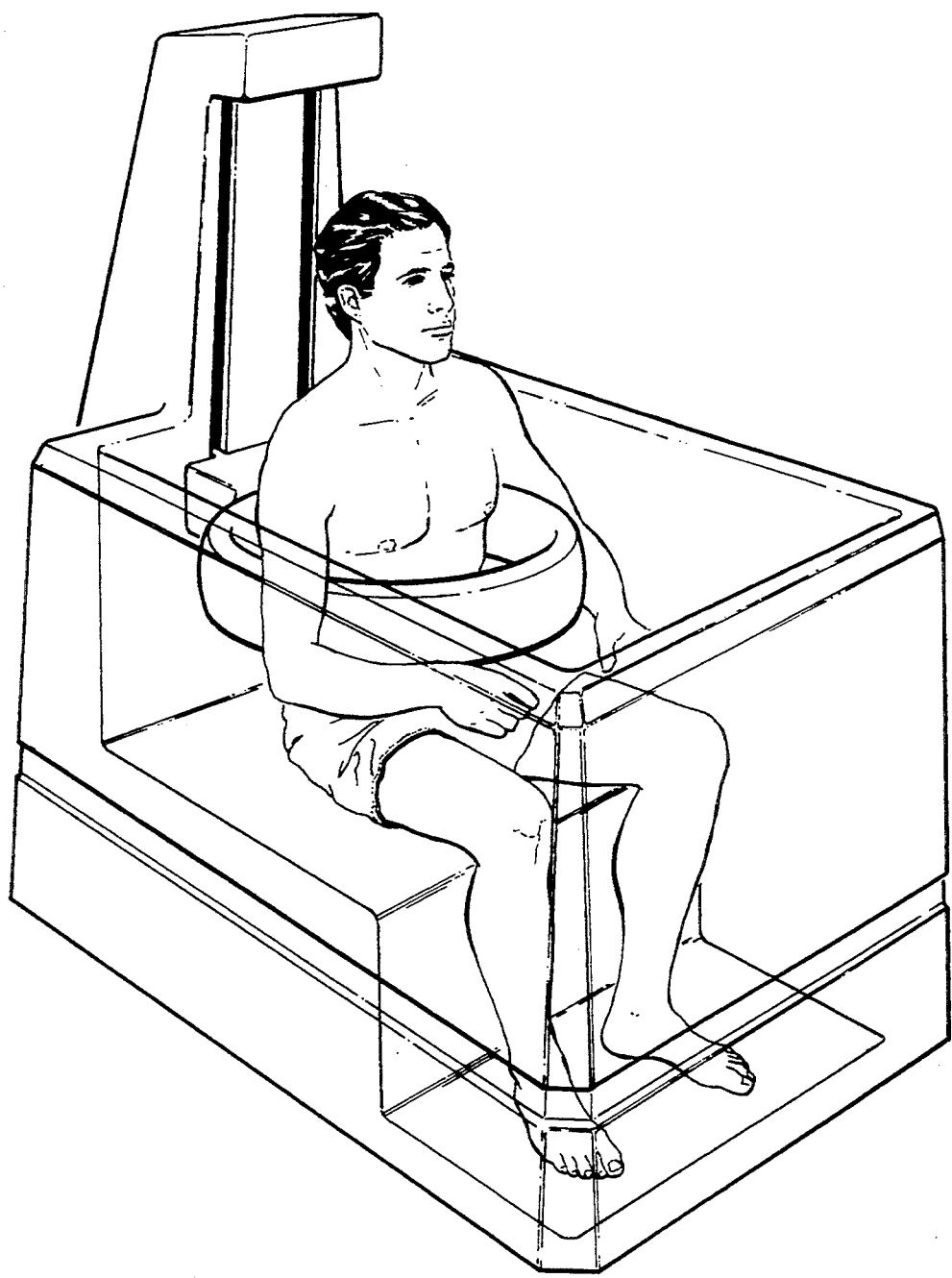
FIG. 14 is an illustration of the invention utilized for abdomen imaging.

Alternate embodiments of the invention also include the geometry of the transducer array. These alternate embodiments may be appropriate to facilitate coupling of the acoustic waves to various parts of the human body including, for example, the abdomen, female breast, cranial cavity, neck, arm and thigh or to other non-human subjects. An embodiment designed to image the abdomen region of human patients is shown in FIG. 14. A device to perform mammography examination is shown in FIG. 13. In this embodiment the ring of 1024 transducers 80 is moveable vertically in an oil tank 82 surrounding water tank 84 so that a complete scan of female breast 86 can be obtained. These images could be viewed separately as shown in FIG. 10 or could be combined in the computer to display a three-dimensional image of the breast. An alternate embodiment includes a similar device to image arteries and veins in arms and legs. Alternate embodiments include a ring of acoustic transducers which do not lie on the locus of a circle, a ring of transducers which do not completely encircle the medium which is to be imaged, a set of transducers which is in segments of various lengths which partially circumscribe the medium, and a set of transducers arranged in parallel rows on opposite sides of the medium to be imaged. Another embodiment which concerns the use of a rubber fluid-filled bladder to couple the acoustic waves from the transducers to the medium which is shown in FIG. 13. Various numbers of transducers could be utilized but the number should be at least eight, and as indicated above, transducers should preferably be spaced no more farther apart than one half wavelength of the acoustic wave being transmitted. For non-circular arrays, the algorithm derived above would have to be recalculated to account for the appropriate boundary conditions.

Alternate embodiments concern the adaptation of the invention to probe medium with electromagnetic waves, with energy spectrums ranging from 1 Hz to x-rays energies, including radiowave, microwave, infrared light, visible light, ultraviolet light imaging devices.

We have tested our prototype at frequency in the range of 500 kHz to 1.25 MHz with good results and we expect that these range could be extended with our technique from 100 kHz to 1.5 MHz.

Although the preferred embodiments described above use the same transducers to broadcast and receive, separate means for broadcasting and receiving could be rotated around the medium to simulate a ring of broadcasting transducers. A similar arrangement could be provided to rotate a receiver to simulate a ring of receiving transducers.

The reader should construe the above described embodiments of this invention as examples and the scope of this invention shall be determined by the appended claim and their legal equivalents.

We claim:

1. An acoustic imaging device for producing a tomographic image along an image slice through a medium defining an average sound speed, said device comprising:
    A) a large number of acoustic transducers located on a circle said large number being greater than $N=2\pi D/\lambda$ where D is the diameter of the circle and $\lambda=0.3$ mm each of said large number of transducers being connected electronically so as to broadcast into said medium an acoustic signal when excited with a periodic signal in the range of 100 kHz to 1.5 MHz and also to produce an electrical signal when excited with an acoustic signal transmitted through said medium,
    B) an electronic signal generation means for generating periodic electronic signals at at least one discrete frequency in the frequency range of 100 kHz to 1.5 MHz said signals being continuous for a time interval of at least D/c where c is the average sound speed of the medium,
    C) a first multiplexing means for applying said periodic electronic signals to a each of said large number of acoustic transducers in order to cause a plurality of said acoustic transducers, one at a time, to broadcast acoustic energy into said medium at a discrete frequency in the frequency range of 100 kHz to 1.5 MHz,
    D) a recording means for recording information carried by electronic transducer signals produced by a plurality of said large number of transducers excited by acoustic energy broadcast transmitted through said medium,
    E) a second multiplexing means for connecting said large number of transducers to said recording means to permit said recording means to record said information carried by said electronic transducer signals, and
    F) a computer means comprising an algorithm for calculating a tomographic image of said medium along said image slice utilizing said information recorded by said recording means.

2. An acoustic imaging device as in claim 1 wherein said at least one identifiable discrete frequency is a plurality of identifiable discrete frequencies.

3. A device as in claim 1 wherein said transducers are equally spaced on said circle.

4. A device as in claim 1 wherein said large number is at least 256.

5. A device as in claim 1 wherein said acoustic recording means comprises a plurality of analog-to-digital converter units each having a buffer memory unit for temporary storage of digital acoustic information.

6. A device as in claim 5 wherein each of said buffer memory units comprise at least one million Bytes of storage capacity.

7. A process for producing a tomographic image of a slice through a medium defining an average speed of sound comprising the steps of:
    A) positioning a large number of transducers on a circle surrounding said medium, said large number being greater than $N=2\pi D/\lambda$ where D is the diameter of the circle and $\lambda=0.3$ mm, said transducers having the capability of broadcasting an acoustic signal into said medium upon being excited with an electrical signal and producing an electrical signal upon being excited with an acoustic signal from said medium,
    B) exciting a plurality of said large number of transducers, one at a time, with an electronic signal defining at least one discrete frequency in order to cause each of said transducers to broadcast, one at a time, into said medium an acoustic signal containing said at least one discrete frequency, each of said acoustic signals being broadcast for a time interval of at least D/c where c is equal to the average speed of sound in said medium said signal to reach an equilibrium in said medium and excite other transducers on said circle to cause them to produce electrical transducer signals carrying information relating to acoustic properties of said medium,
    C) record information carried by said electrical transducer signals from said large number of transducers,
    D) using said recorded information calculate with a computer said tomographic image of said image slice of said medium.

8. A process as in claim 7 wherein said at least one identifiable discrete frequency is a plurality of identifiable discrete frequencies.

9. A process as in claim 6 comprising the additional step of producing a plurality of said tomographic images of said image slices of said medium.

10. A process as in claim 9 comprising the additional step of producing a plurality of said tomographic images of said image slices of said medium said image slices being parallel to each other and equally spaced along said medium.

11. A process as in claim 10 comprising the additional step of producing a plurality of said tomographic images of said image slices of said medium said image slices being parallel to each other and equally spaced along said medium and said image slices overlapping each other.

12. A process as in claim 11 comprising the additional step of forming a three-dimensional image from said tomographic images of said image slices.

13. A process as in claim 7 wherein said medium includes human tissue and comprising the following additional steps for monitoring the placement of a biopsy needle in said tissue:
   A) calculate a sufficient number of tomographic images of said medium in order to identify a biopsy location,
   B) insert a biopsy needle to said biopsy location,
   D) calculate at least one tomographic image of said medium with said needle at said biopsy location,
   E) verify that said biopsy needle is at said location, and
   F) remove biopsy sample with said biopsy needle.

14. A process as in claim 7 comprising the following additional steps for measuring temperature distributions of said medium comprising:
   A) locally heat at least a portion of said image slice of said medium,
   B) calculate second said tomographic image of said image slice of said medium, and
   C) subtract first said tomographic image from said second tomographic image to produce a final image representing the effect of heating the medium.

15. A process as in claim 7 comprising the additional steps of measuring temperature distributions of said medium comprising:
   A) locally heat at least a portion of said image slice of said medium,
   B) calculate second said tomographic image of said image slice of said medium, and
   C) divide first said tomographic image from said second tomographic image to produce a final image representing the effect of heating the medium.

16. A process as in claim 7 wherein said medium comprises at least some portion of the human body.

17. A process as in claim 7 wherein said medium comprises the human female breast.

18. A process as in claim 7 wherein said medium comprises the human abdomen.

* * * * *